US009106848B2

(12) United States Patent
Kamo

(10) Patent No.: US 9,106,848 B2
(45) Date of Patent: Aug. 11, 2015

(54) OPTICAL UNIT AND ENDOSCOPE INCLUDING THE OPTICAL UNIT

(71) Applicant: Olympus Medical Systems Corp., Tokyo (JP)

(72) Inventor: Yuji Kamo, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 326 days.

(21) Appl. No.: 13/686,398

(22) Filed: Nov. 27, 2012

(65) Prior Publication Data

US 2013/0155212 A1    Jun. 20, 2013

Related U.S. Application Data

(63) Continuation of application No. PCT/JP2012/063433, filed on May 25, 2012.

(30) Foreign Application Priority Data

Jun. 6, 2011    (JP) .................................. 2011-126547

(51) Int. Cl.
*H04N 7/18*    (2006.01)
*H04N 5/335*    (2011.01)
(Continued)

(52) U.S. Cl.
CPC ............ *H04N 5/335* (2013.01); *A61B 1/00006* (2013.01); *A61B 1/00096* (2013.01); *A61B 1/00186* (2013.01); *A61B 1/00188* (2013.01); *A61B 1/051* (2013.01); *A61B 5/0031* (2013.01); *G02B 23/243* (2013.01); *G02B 27/0018* (2013.01); *H04N 7/18* (2013.01); *G02B 5/208* (2013.01)

(58) Field of Classification Search
USPC .......................................................... 348/65
See application file for complete search history.

(56) References Cited

U.S. PATENT DOCUMENTS 5,587,839 A    12/1996    Miyano et al.
2009/0161234 A1    6/2009    Sasamoto
(Continued)

FOREIGN PATENT DOCUMENTS

EP    2131225    12/2009
JP    09-054225    2/1997
(Continued)

OTHER PUBLICATIONS

Extended European Search Report, dated Oct. 8, 2014, issued in corresponding European Patent Application No. 12796758.6.
(Continued)

*Primary Examiner* — Dave Czekaj
*Assistant Examiner* — Leron Beck
(74) *Attorney, Agent, or Firm* — Kenyon & Kenyon LLP

(57) ABSTRACT

An optical unit includes: a plurality of lenses that form an object image on an image plane that is a light-receiving surface of a CCD; an aperture diaphragm; and an infrared absorption filter disposed on the image plane side relative to the aperture diaphragm, the infrared absorption filter including coating surfaces resulting from a YAG laser cut-off film and an LD laser cut-off film that each cut off predetermined laser light being formed respectively, and an F number FNO, a maximum image height IH, and a distance $\Delta d$ between a paraxial image formation position in a ghost optical path on which a light beam emitted from the aperture diaphragm BI is reflected by the image plane and further reflected by the coating surface and reaches the image plane again and the image plane satisfy (Expression 1):

$0.75 < |FNO \cdot IH/\Delta d| < 2.0$    (Expression 1).

11 Claims, 5 Drawing Sheets

(51) Int. Cl.
  *G02B 23/24* (2006.01)
  *G02B 27/00* (2006.01)
  *A61B 5/00* (2006.01)
  *A61B 1/00* (2006.01)
  *A61B 1/05* (2006.01)
  *G02B 5/20* (2006.01)

(56) References Cited

U.S. PATENT DOCUMENTS

2009/0237807 A1  9/2009  Sasamoto
2010/0142058 A1  6/2010  Takato

FOREIGN PATENT DOCUMENTS

| JP | 10-113329 | 5/1998 |
| JP | 11-076146 | 3/1999 |
| JP | 200420972 A | 1/2004 |
| JP | 2009-093198 | 4/2009 |
| JP | 2009-151191 | 7/2009 |
| JP | 2009-223183 | 10/2009 |
| JP | 2009-294496 | 12/2009 |

OTHER PUBLICATIONS

International Search Report, issued in corresponding International Application No. PCT/JP2012/063433.

OPTICAL UNIT AND ENDOSCOPE INCLUDING THE OPTICAL UNIT

CROSS REFERENCE TO RELATED APPLICATION

This application is a continuation application of PCT/JP2012/063433 filed on May 25, 2012 and claims benefit of Japanese Application No. 2011-126547 filed in Japan on Jun. 6, 2011, the entire contents of which are incorporated herein by this reference.

BACKGROUND OF THE INVENTION

1. Field of the Invention

The present invention relates to an optical unit and an endoscope including the optical unit.

2. Description of the Related Art

Endoscopes are used for observation of an inside of a subject that cannot be observed from an outside. In the case of electronic endoscopes, in a distal end portion of an insertion portion, which is to be inserted into a body cavity, a CCD (charge coupled device) is incorporated together with an optical unit (image-formation optical system). Because a CCD has a relatively high sensitivity to infrared light, an optical unit including an infrared light cut-off filter is used for proper color reproduction.

On the other hand, endoscopes are used not only for observation but also for therapy. For example, with an endoscope apparatus including a laser therapy device, e.g., incision of a diseased site is performed using a laser. When therapy using laser light with an infrared wavelength is performed, light reflected from a site subjected to the therapy is very intense and thus cannot sufficiently be cut off by an infrared light cut-off filter, and a resulting observation screen is extremely bright, which may make observation of an object image difficult. Therefore, in the optical unit, a laser light cut-off filter that cuts off (blocks) laser light for therapy is arranged in addition to the infrared light cut-off filter.

Here, Japanese Patent Application Laid-Open Publication Nos. 9-54255, 10-113329 and 11-76146 each disclose an optical unit for an endoscope using a multi-layer interference film (cut-off coat) using the effect of interference of light as a laser light cut-off filter.

On the other hand, Japanese Patent Application Laid-Open Publication No. 2009-93198 discloses that in, e.g., a general video camera, an optical system (optical unit) having predetermined specifications is used in order to reduce periodic pattern ghost generation attributable to a plurality of light-receiving elements included in an image pickup device being arranged in a predetermined periodic pattern.

SUMMARY OF THE INVENTION

An optical unit according to an embodiment includes: a plurality of lenses that form an object image on an image plane that is a light-receiving surface of a solid-state image pickup device; an aperture diaphragm; and an optical member disposed on the image plane side relative to the aperture diaphragm, the optical member including a coating surface resulting from a multi-layer interference film that transmits visible light and cuts off light having a particular wavelength being formed thereon, and an F number FNO, a maximum image height IH, and a distance $\Delta d$ between a paraxial image formation position in a ghost optical path on which a light beam emitted from the aperture diaphragm is reflected by the image plane and further reflected by the coating surface and reaches the image plane again and the image plane satisfy (Expression 1):

$$0.75 < |FNO \cdot IH / \Delta d| < 2.0 \quad \text{(Expression 1)}.$$

Also, an endoscope according to another embodiment includes: an optical unit including a plurality of lenses that form an object image on an image plane that is a light-receiving surface of a solid-state image pickup device, an aperture diaphragm, and an optical member disposed on the image plane side relative to the aperture diaphragm, the optical member including a coating surface resulting from a multi-layer interference film that transmits visible light and cuts off light having a particular wavelength being formed thereon, wherein an F number FNO, a maximum image height IH, and a distance $\Delta d$ between a paraxial image formation position in a ghost optical path on which a light beam emitted from the aperture diaphragm is reflected by the image plane and further reflected by the coating surface and reaches the image plane again and the image plane satisfy (Expression 1), $$0.75 < |FNO \cdot IH / \Delta d| < 2.0 \quad \text{(Expression 1)};$$

a solid-state image pickup device; and an illumination optical system.

DETAILED DESCRIPTION OF THE PREFERRED EMBODIMENTS

First Embodiment

Figure 1:
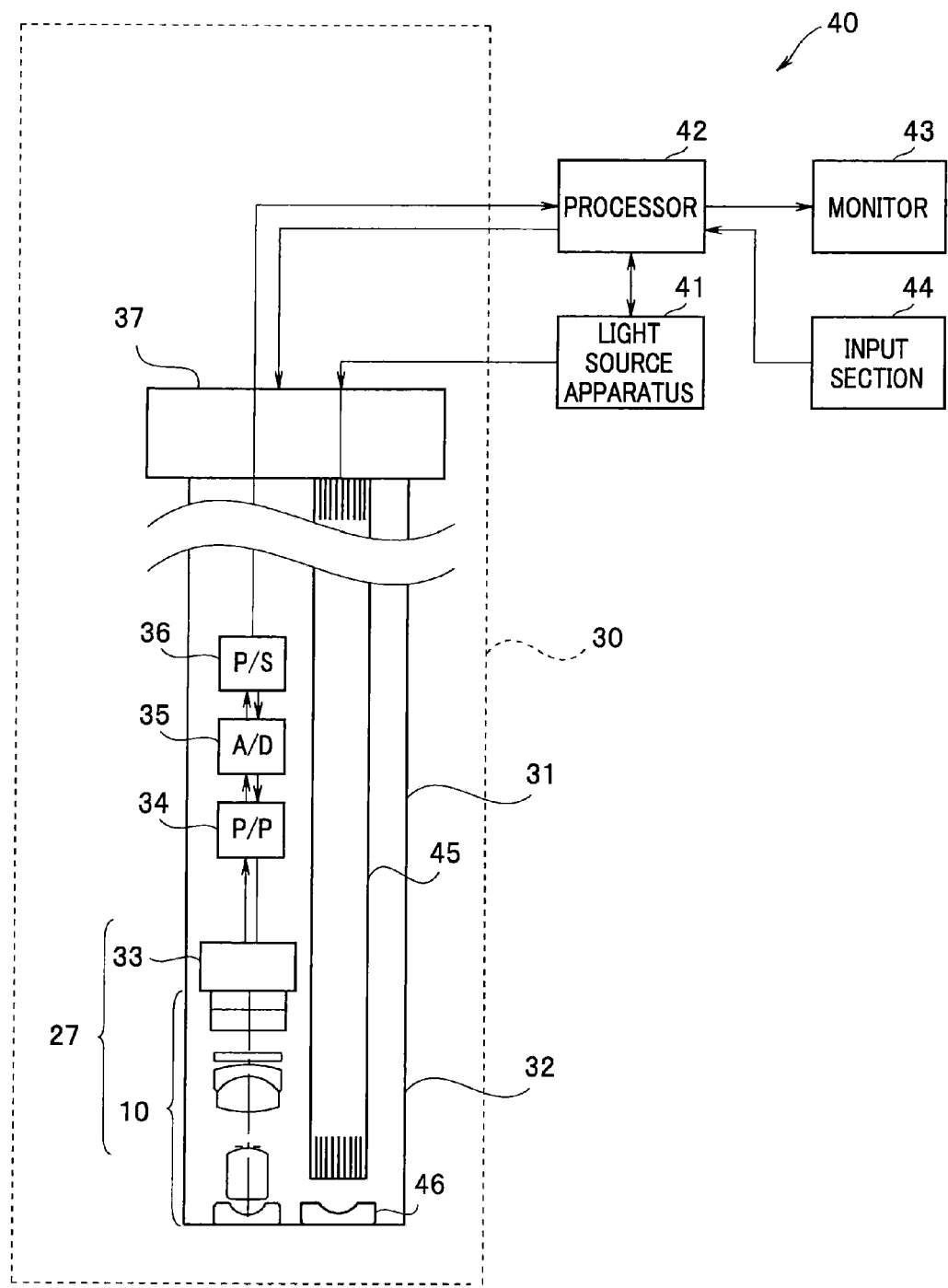
FIG. 1 is a diagram of a configuration of an endoscope according to a first embodiment.

First, an optical unit 10 according to a first embodiment and an endoscope 30 including the optical unit 10 will be described. As illustrated in FIG. 1, the endoscope 30 forms an endoscope system 40 jointly with a light source apparatus 41 and a processor 42. The endoscope 30 includes an insertion portion 31 to be inserted into the body of a subject. The light source apparatus 41 generates illuminating light that illuminates the inside of the body. The processor 42 performs various types of signal processing and performs control of the endoscope system 40.

Inside the insertion portion 31 of the endoscope 30, light guide fibers 45 that guide illuminating light from the light source apparatus 41 to a distal end portion 32 is inserted to illuminate the inside of the body via an illumination optical system 46. Note that FIG. 1 illustrates only an object-side lens in the illumination optical system 46.

The processor 42 can be used as an endoscope system suitable for a purpose in combination with any of various types of endoscopes and any of various types of light source apparatuses. Furthermore, the endoscope system 40 includes a monitor 43 that displays, e.g., an endoscopic image, and an input section 44 such as a keyboard via which a surgeon, e.g., makes settings.

The endoscope 30 is an electronic endoscope including a CCD 33, which is a solid-state image pickup device that photographs a color endoscopic image, in the distal end portion 32 of the insertion portion 31 connected to an operation portion 37, a preprocessing (P/P) section 34, an A/D conversion section 35, and a parallel-serial conversion (P/S) section 36. In the distal end portion 32, the optical unit 10, which is an image-formation optical system for forming an optical image, and the CCD 33 that photographs the inside of a subject are arranged, and an endoscopic image photographed by the CCD 33 is converted into a digital signal and transmitted to the processor 42.

The CCD 33 includes a light-receiving surface (image plane) in which a number of light-receiving elements, the number corresponding to a number of pixels, are arranged in a matrix (vertically/horizontally) with a predetermined pitch (pixel pitch) p.

Figure 2:
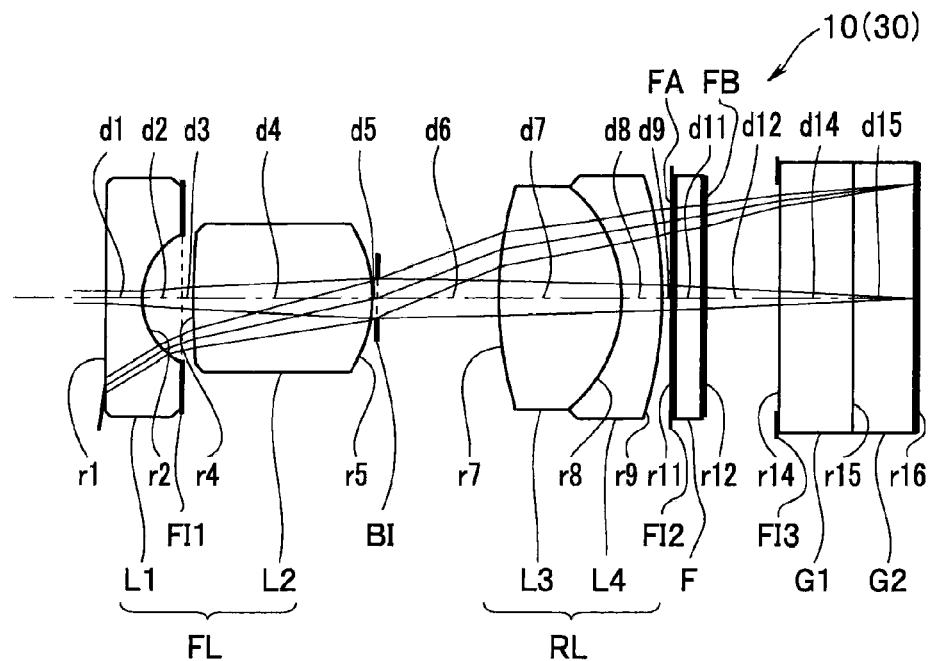
FIG. 2 is a cross-sectional diagram along an optical axis for illustrating an optical unit according to the first embodiment.
Figure 3:
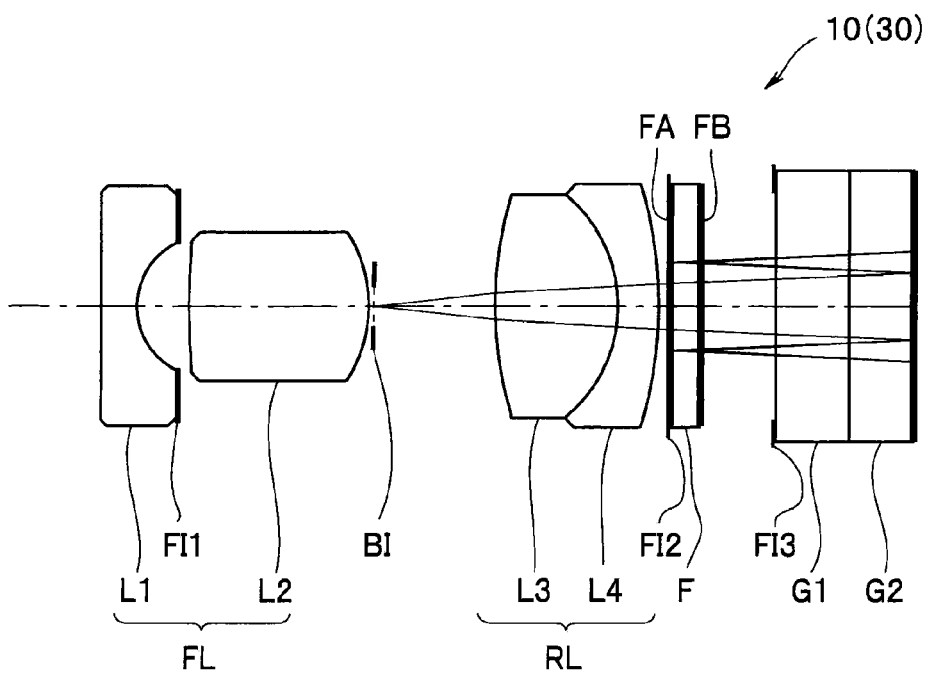
FIG. 3 is a cross-sectional diagram along a ghost optical path in the optical unit according to the first embodiment.

As illustrated in FIGS. 2 and 3, the optical unit 10 includes a front lens group LF (a plano-concave first negative lens L1 and a biconvex second positive lens L2), an aperture diaphragm BI, a rear lens group LB (a biconvex third positive lens L3 and a fourth negative lens L4 that is convex toward the image plane side), which is a positive lens group, an infrared absorption filter F, a cover glass G1, and a CCD cover glass G2 in this order from the object side. Note that the third positive lens L3 and the fourth negative lens L4 are joined together and the cover glass G1 and the CCD cover glass G2 are joined together, respectively. Also, reference numeral FI1 denotes a flare diaphragm.

The infrared absorption filter F includes a parallel-plate optical member that absorbs and cuts off light in an infrared region. Furthermore, on the object side of the infrared absorption filter F, a YAG laser cut-off film (coating) FA is disposed while on the image plane side of the infrared absorption filter F, an LD laser cut-off film (coating) FB is disposed.

Each of the YAG laser cut-off film FA and the LD laser cut-off film FB is a multi-layer interference film that transmits visible light and cuts off light having a particular wavelength, that is, particular laser light other than visible light. When therapy is provided using YAG laser, the YAG laser cut-off film FA cuts off YAG laser light (with a wavelength of 1060 nm) entering the CCD 33. When therapy is provided using LD laser, the LD laser cut-off film FB cuts off LD laser light (with a wavelength of 810 nm) entering the CCD 33.

Each of the YAG laser cut-off film FA and the LD laser cut-off film FB has a multi-layer structure, and has a low transmittance for a predetermined wavelength region due to the effect of interference of light, but has a high reflectance for light with wavelengths other than the wavelengths in that region, and thus, intense reflection occurs at the coating surface.

As already described, a part of light entering the CCD 33 is reflected by the light-receiving surface (image plane). Since a plurality of light-receiving elements are regularly arranged in two dimensions on the light-receiving surface of the CCD 33, reflected light becomes diffracted light including primary light, secondary light . . . with zero-order light as a center thereof, the diffracted light being bright in a plurality of particular directions in two dimensions, due to diffraction phenomenon. The diffracted light is reflected again by the coating surfaces and enters the CCD 33, resulting in generation of a periodic pattern ghost.

In other words, in the optical unit 10, diffracted light from the CCD 33 is intensely reflected by the laser cut-off films FA and FB each having a high reflectance for a visible light region, and thus, a periodic pattern ghost in which a plurality of circular ghosts are regularly arranged vertically and horizontally is generated easily.

Here, each of the individual ghosts in the periodic pattern ghost has a circular shape because each of the individual ghosts is an image resulting from an image of a shape of the aperture diaphragm BI being formed. In other words, a periodic pattern ghost is generated according to a positional relationship among the aperture diaphragm BI, the light-receiving surface (image plane) of the CCD 33 and the coating surfaces of the laser cut-off films. In other words, a periodic pattern ghost is generated according to a relationship in image formation in a ghost optical path on which a light beam emitted from the aperture diaphragm BI is reflected by the image plane and further reflected by the coating surfaces and reaches the image plane again, with the aperture diaphragm BI as an object point.

In other words, as illustrated in FIG. 3, the amount of light in the ghost optical path on which a light beam emitted from the aperture diaphragm BI is reflected by the image plane of the CCD 33 and further reflected by the coating surfaces (the YAG laser cut-off film FA and the LD laser cut-off film FB) and reaches the image plane again easily becomes intense.

A periodic pattern ghost gives a strong feeling of discomfort to a user compared to normal ghosts or flares and in addition, is generated over a relatively wide range, causing a problem in observation. Hereinafter, "periodic pattern ghost" is simply referred to as "ghost."

In particular, in the optical unit 10 in the endoscope 30, as opposed to, e.g., general video cameras, intense light is frequently generated on an image pickup screen, that is, intense light frequently falls on the image plane of the CCD 33. This is because the optical unit 10 includes an illumination optical system 46 for illuminating the inside of a body cavity. When illuminating light from the distal end portion 32 is reflected by, in particular, metal forceps used for treatment, intense light is generated on the screen. In other words, since the endoscope 30 includes the illumination optical system 46, intense light easily enters the optical unit 10.

However, as described later, in the optical unit 10, periodic pattern ghost generation is effectively reduced.

Here, numerical data, etc., of the optical members included in the optical unit 10 are indicated. In the numerical data, r is a curvature radius of the respective surface, d is a thickness of the respective optical member or an air space between the respective optical members, n is a reflectance of the respective optical member for the e-line, ν is an Abbe number of the respective optical member for the e-line, and FNO represents an F number. The units of r and d and the like are mm.

Note that these symbols are used in common in numerical data, etc., for the other embodiments, which will be described later.

Numerical data of the optical unit 10 according to the first embodiment are indicated in (Table 1).

An FNO is 7.794, a half angle of view is 81.27 degrees, a maximum image height IH is 1.226 mm, a pixel pitch p is 0.0032 mm (3.2 μm), a diameter Ds of the aperture diaphragm BI is 0.426 mm, a difference Δd between the image plane and a paraxial image formation position in the ghost optical path is −10.13 mm (for FA) and is −9.7 mm (for FB), a paraxial imaging magnification β is 1.795 (for FA and FB), a rear lens group RL is a positive lens group, and a focal length f1 thereof is 4.09 mm.

TABLE 1

| Surface number | Curvature radius (r) | Surface interval (d) | Refractive index (n) | Abbe number (v) | |
|---|---|---|---|---|---|
| 1 | ∞ | 0.3861 | 1.8830 | 40.76 | L1 |
| 2 | 0.7781 | 0.4267 | | | |
| 3 | | 0.1409 | | | FI1 (Flare diaphragm) |
| 4 | 10.3308 | 1.9426 | 1.6700 | 47.23 | L2 |
| 5 | −1.4448 | 0.0531 | | | |
| 6 | | 1.3241 | | | BI (Aperture diaphragm) |
| 7 | 4.1887 | 1.3364 | 1.7292 | 54.68 | L3/L4 |
| 8 | −1.5405 | 0.4471 | 1.9229 | 18.90 | |
| 9 | −4.3799 | 0.1177 | | | |
| 10 | | 0 | | | FI2 (Flare diaphragm) |
| 11 | ∞ | 0.3316 | 1.5140 | 75.00 | F (YAG cut-off) |
| 12 | ∞ | 0.8415 | | | (LD cut-off) |
| 13 | | 0 | | | FI3 (Flare diaphragm) |
| 14 | ∞ | 0.7990 | 1.5163 | 64.14 | G1/G2 |
| 15 | ∞ | 0.6956 | 1.5051 | 63.26 | |
| 16 (Image plane) | ∞ | 0 | | | |

Modifications of the First Embodiment

Figure 4:
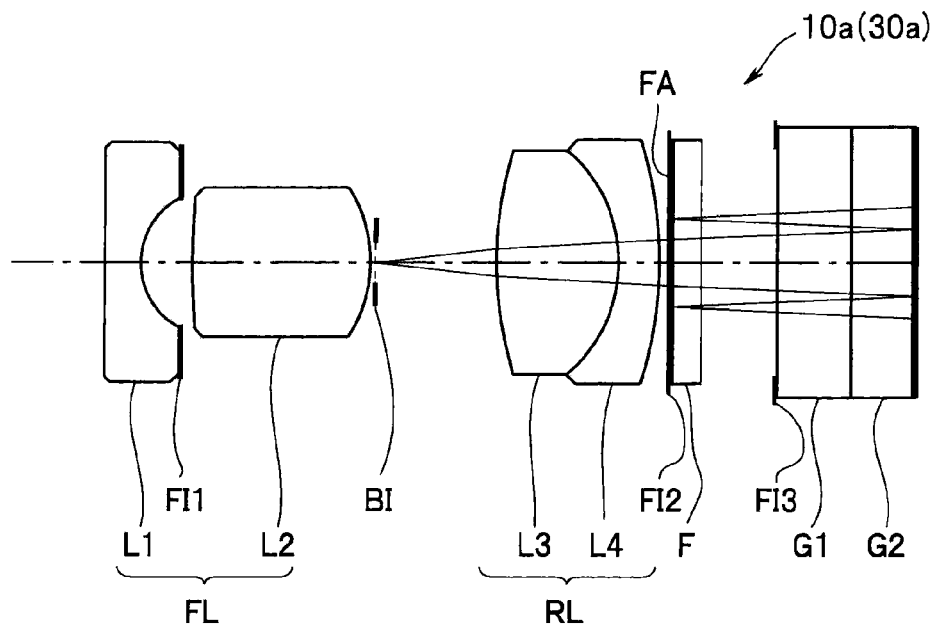
FIG. 4 is a cross-sectional diagram along a ghost optical path in an optical unit according to modification 1 of the first embodiment.
Figure 5:
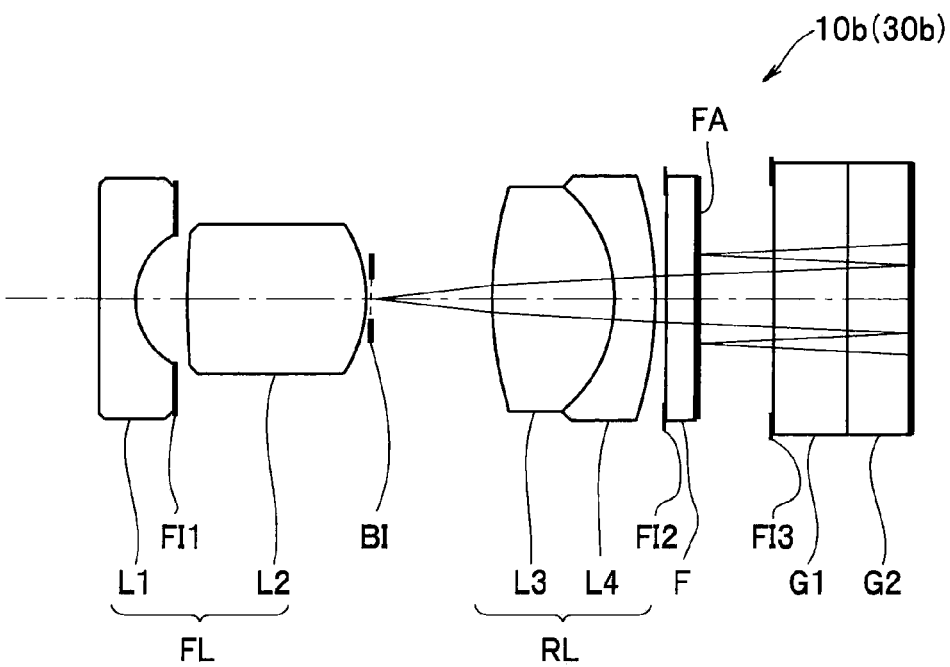
FIG. 5 is a cross-sectional diagram along a ghost optical path in an optical unit according to modification 2 of the first embodiment.

The optical unit 10 according to the first embodiment includes the coatings FA and FB on the opposite surfaces of the infrared absorption filter F. On the other hand, an optical unit 10a in an endoscope 30a according to modification 1, which is illustrated in FIG. 4, includes a laser cut-off film FA only on the object side of an infrared absorption filter F. Also, an optical unit 10b in an endoscope 30b according to modification 2, which is illustrated in FIG. 5, includes a laser cut-off film FA only on the image plane side of an infrared absorption filter F.

Numerical data, etc., of each of the optical unit 10a and the optical unit 10b are similar to those of the optical unit 10.

Second Embodiment

Figure 6:
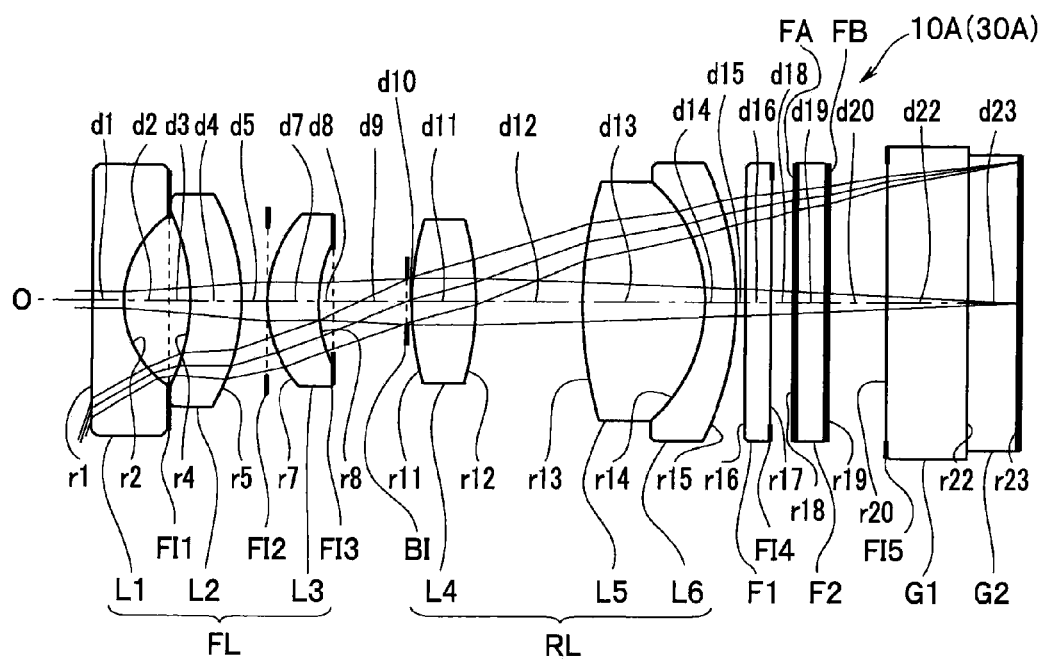
FIG. 6 is a cross-sectional diagram along an optical axis for illustrating an optical unit according to a second embodiment.
Figure 7:
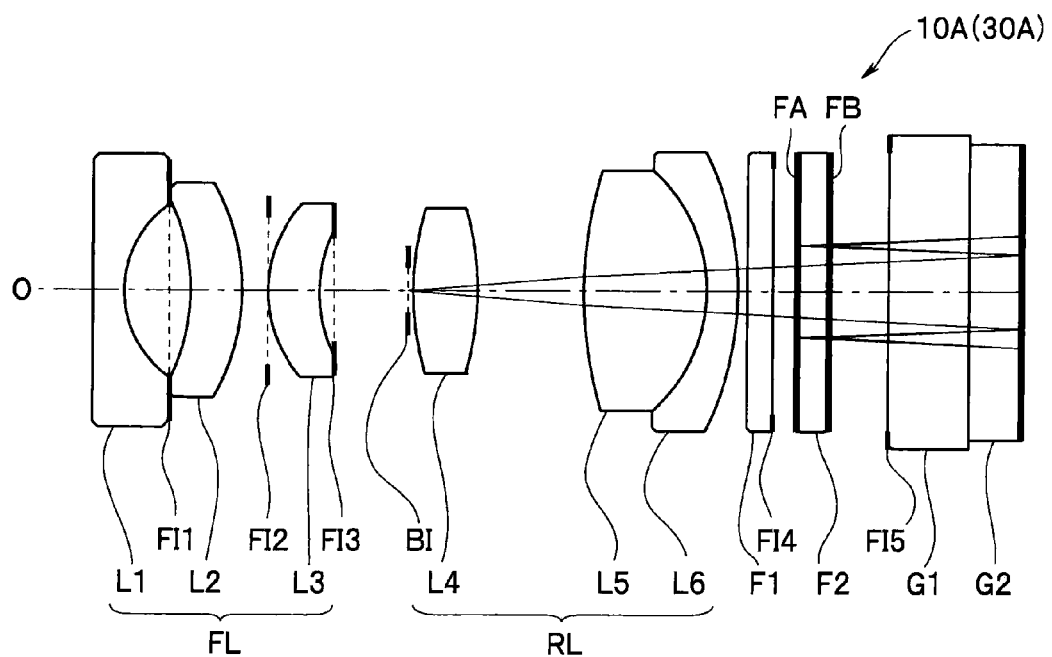
FIG. 7 is a cross-sectional diagram along a ghost optical path in the optical unit according to the second embodiment.

As illustrated in FIGS. 6 and 7, an optical unit 10A in an endoscope 30A according to a second embodiment includes a front lens group FL (a plano-concave first negative lens L1, a second positive lens L2 that is convex toward the image plane side and a third positive lens L3 that is convex toward the object side), an aperture diaphragm BI, a rear lens group RL (a biconvex fourth positive lens L4, a biconvex fifth positive lens L5 and a sixth negative lens L6 that is convex toward the image plane side), an infrared absorption filter F1, a filter F2, a cover glass G1 and a CCD cover glass G2 in this order from the object side. The fifth positive lens L5 and the sixth negative lens L6 are joined together and the cover glass G1 and the CCD cover glass G2 are joined together, respectively. Furthermore, reference numerals FI1 to FI4 denote flare diaphragms.

On the object side of the filter F2, an LD laser light cut-off film FA is formed while on the image plane side of the filter F2, a YAG laser light cut-off film FB is formed. The third positive lens L3 is movable in an optical axis direction for focusing.

Numerical data of the optical unit 10A according to the second embodiment are indicated in (Table 2).

An FNO is 8.023 (at the time of far point focusing) to 7.733 (at the time of near point focusing), a half angle of view is 71.61 degrees (at the time of far point focusing) to 71.25 degrees (at the time of near point focusing), a maximum image height IH is 1.604 mm, a pixel pitch p is 2.8 μm, a diameter Ds of the aperture diaphragm BI is 0.514 mm, a difference Δd between the image plane and a paraxial image formation position in a ghost optical path is −10.69 mm (for FA at the time of far point focusing and at the time of near point focusing), and is −10.19 mm (for FB at the time of far point focusing and at the time of near point focusing), a paraxial imaging magnification β is 1.628 (for FA and FB), the rear lens group RL is a positive lens group and a focal length f1 thereof is 2.86 mm.

TABLE 2

| Surface number | Curvature radius (r) | Surface interval (d) | Refractive index (n) | Abbe number (v) | |
|---|---|---|---|---|---|
| 1 | ∞ | 0.3559 | 1.883 | 40.76 | L1 |
| 2 | 1.1780 | 0.5207 | | | |
| 3 | | 0.2523 | | | FI1 (Flare diaphragm) |
| 4 | −2.2561 | 0.6059 | 1.883 | 40.76 | L2 |
| 5 | −2.3581 | 0.30037-0.80301 | | | |
| 6 | | 0 | | | FI2 (Flare diaphragm) |
| 7 | 1.4023 | 0.5976 | 1.581 | 40.75 | L3 |
| 8 | 1.6261 | 0.1821 | | | |
| 9 | | 0.84471-0.35926 | | | FI3 (Flare diaphragm) |
| 10 | | 0.0572 | | | BI (Aperture diaphragm) |
| 11 | 3.0624 | 0.7590 | 1.487 | 70.23 | L4 |
| 12 | −3.0624 | 1.2358 | | | |
| 13 | 4.6930 | 1.4086 | 1.487 | 70.23 | L5/L6 |
| 14 | −1.7947 | 0.3633 | 1.923 | 18.90 | |
| 15 | −3.5088 | 0.1132 | | | |
| 16 | ∞ | 0.2915 | 1.514 | 75.00 | F1 |
| 17 | ∞ | 0 | | | |
| 18 | | 0.2786 | | | FI4 (Flare diaphragm) |
| 19 | ∞ | 0.3763 | 1.523 | 58.50 | F2 (LD cut-off) (YAG cut-off) |
| 20 | ∞ | 0.6738 | | | |
| 21 | | 0 | | | FI5 (Flare diaphragm) |
| 22 | ∞ | 0.9513 | 1.516 | 64.14 | G1/G2 |
| 23 | ∞ | 0.6050 | 1.505 | 63.26 | |
| 24 (Image plane) | ∞ | 0 | | | |

Third Embodiment

Figure 8:
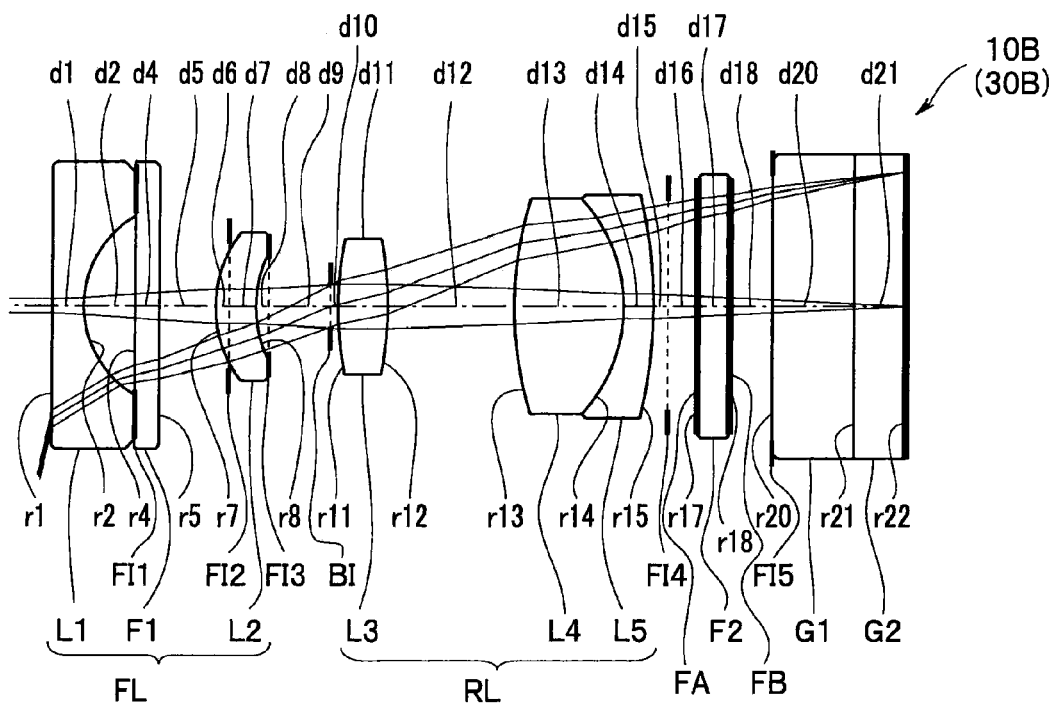
FIG. 8 is a cross-sectional diagram along an optical axis for illustrating an optical unit according to a third embodiment.
Figure 9:
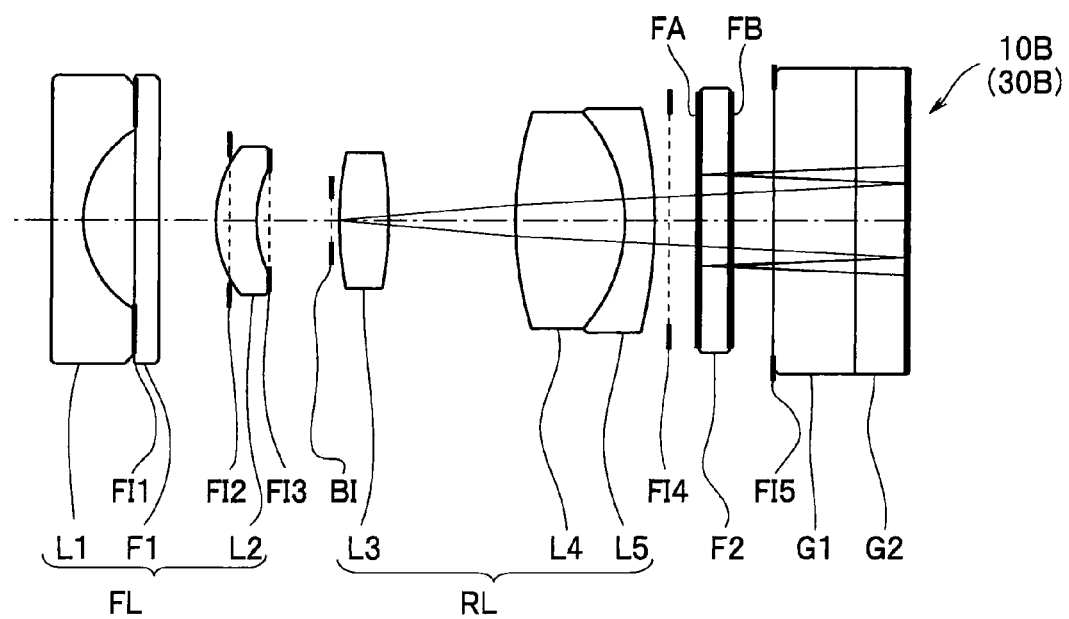
FIG. 9 is a cross-sectional diagram along a ghost optical path in the optical unit according to the third embodiment.

As illustrated in FIGS. 8 and 9, an optical unit 10B in an endoscope 30B according to a third embodiment includes a front lens group FL (a plano-concave first negative lens L1, an infrared absorption filter F1 and a second positive lens L2) that is convex toward the object side, an aperture diaphragm BI, a rear lens group RL (a biconvex third positive lens L3, a biconvex fourth positive lens L4 and a fifth negative lens L5 that is convex toward the image plane side), a filter F2, a cover glass G1 and a CCD cover glass G2 in this order from the object side. The fourth positive lens L4 and the fifth negative lens L5 are joined together and the cover glass G1 and the CCD cover glass G2 are joined together, respectively. Also, reference numerals FI1 to FI5 are flare diaphragms.

On the object side of the filter F2 that is a transparent parallel plate, an LD laser light cut-off film FA is formed while on the image plane side of the filter F2, a YAG laser light cut-off film FB is formed. The second positive lens L2 is movable in an optical axis direction for focusing.

Numerical data of the optical unit 10B according to the third embodiment are indicated in (Table 3).

An FNO is 7.872 (at the time of far point focusing) to 7.582 (at the time of near point focusing), an half angle of view is 77.51 degrees (at the time of far point focusing) to 73.29 degrees (at the time of near point focusing), a maximum image height IH is 1.486 mm, a pixel pitch p is 0.00265 mm (2.65 μm), a diameter Ds of the aperture diaphragm BI is 0.478 mm, a difference Δd between the image plane and a paraxial image formation position in a ghost optical path is −9.93 mm (for FA at the time of far point focusing and at the time of near point focusing) and is −8.85 mm (for FB at the time of far point focusing and at the time of near point focusing), a paraxial imaging magnification β is 1.554 (for FA and FB), the rear lens group RL is a positive lens group, and a focal length f1 thereof is 2.33 mm.

TABLE 3

| Surface number | Curvature radius (r) | Surface interval (d) | Refractive index (n) | Abbe number (v) | |
|---|---|---|---|---|---|
| 1 | ∞ | 0.3456 | 1.883 | 40.76 | L1 |
| 2 | 1.1467 | 0.5826 | | | |
| 3 | | 0 | | | FI1 (Flare diaphragm) |
| 4 | ∞ | 0.276 | 1.514 | 75.00 | F1 |
| 5 | ∞ | 0.79512–1.27232 | | | |
| 6 | | −0.1423 | | | FI2 (Flare diaphragm) |
| 7 | 1.3561 | 0.4538 | 1.773 | 49.60 | L2 |
| 8 | 1.4495 | 0.1402 | | | |
| 9 | | 0.70675–0.22957 | | | FI3 (Flare diaphragm) |
| 10 | | 0.0814 | | | BI (Aperture diaphragm) |
| 11 | 3.6271 | 0.5640 | 1.729 | 54.68 | L3 |
| 12 | −3.6271 | 1.4253 | | | |
| 13 | 4.1298 | 1.2210 | 1.589 | 61.14 | L4/L5 |
| 14 | −1.7563 | 0.3378 | 1.923 | 18.90 | |
| 15 | −5.0543 | 0.1654 | | | |
| 16 | | 0.3257 | | | FI4 (Flare diaphragm) |
| 17 | ∞ | 0.3641 | 1.523 | 59.89 | F2 (LD cut-off) |
| 18 | ∞ | 0.4939 | | | (YAG cut-off) |
| 19 | | 0 | | | FI5 (Flare diaphragm) |
| 20 | ∞ | 0.9046 | 1.516 | 64.14 | G1/G2 |
| 21 | ∞ | 0.5720 | 1.506 | 60.00 | |
| 22 (Image plane) | ∞ | 0 | | | |

As a result of studies on various optical units including the above embodiments and modifications, the inventors found that an optical unit that meets the following conditions can provide substantial periodic pattern ghost reduction.

<Condition 1>

It is most important that a position where a ghost is in focus is set in a position far from the image plane, that is, a ghost is what is called "blurred," to diffuse ghost light. Therefore, an optical unit requires an F number FNO, a maximum image height IH and a distance Δd between a paraxial image formation position in a ghost optical path on which a light beam emitted from the aperture diaphragm BI is reflected by the image plane and further reflected by the coating surfaces and reaches the image plane again and the image plane to satisfy (Expression 1):

$$0.75<|FNO \cdot IH/\Delta d|<2.0 \quad \text{(Expression 1)}.$$

If the value is less than the upper limit in (Expression 1) an increase in total length of the optical unit is prevented, and if the value exceeds the lower limit in the above expression, the ghost is out of focus, and thus, visibility deterioration is prevented and, e.g., erroneous recognition of the ghost as a small affected part is prevented.

Note that the optical unit more preferably satisfies (Expression 1A) and particularly preferably satisfies (Expression 1B) to make the aforementioned effect more prominent:

$$0.85<|FNO \cdot IH/\Delta d|<1.7 \quad \text{(Expression 1A); and}$$

$$0.90<|FNO \cdot IH/\Delta d|<1.4 \quad \text{(Expression 1B)}.$$

<Condition 2>

Next, for the optical unit, it is preferable that a position of a ghost in a screen be set on the side that is the same as the side where a light source image that is a cause of the ghost is positioned with respect to a center point of the screen to obscure the ghost. Furthermore, it is preferable that each of ghosts included in a periodic pattern ghost be enlarged to form large images of the ghosts to diffuse the light of the ghost.

Thus, it is preferable that in the optical unit, the maximum image height IH, a diameter Ds of the aperture diaphragm BI and a paraxial linear magnification β for the ghost optical path on which a light beam emitted from the aperture diaphragm BI is reflected by the image plane and further reflected by the coating surfaces and reaches the image plane again satisfy (Expression 2):

$$0.10<\beta \cdot Ds/IH<1.2 \quad \text{(Expression 2)}.$$

If the value is less than the upper limit in the above expression, neither an increase in total length of the optical unit nor deterioration in workability of the lenses occurs. If the value exceeds the lower limit in the above expression, the ghost on the image screen is low in brightness and thus inconspicuous because of the large magnification.

Furthermore, a paraxial linear magnification β satisfying the above expression is a positive value. In a CCD screen, if the paraxial linear magnification β is a positive value (+), a ghost is generated on the side that is the same as the side where a light source image that is a cause of the ghost with respect to a center of the screen, and if the paraxial linear magnification β is a negative value (−), a ghost is generated on the side opposite to the side where a light source image that is a cause of the ghost with respect to the center of the screen.

Note that the optical unit more preferably satisfies (Expression 2A) and particularly preferably satisfies (Expression 2B) to make the aforementioned effect more prominent:

$$0.20<\beta \cdot Ds/IH<1.0 \quad \text{(Expression 2A); and}$$

$$0.35<\beta \cdot Ds/IH<0.7 \quad \text{(Expression 2B)}.$$

In particular, satisfaction of <Condition 1> and <Condition 2> enables proper and simultaneous setting of a focal position and a magnification for the optical unit.

<Condition 3>

Furthermore, it is preferable that in the optical unit, a distance D2 from each of the coating surfaces to the image plane and a focal length f1 of a rear lens group RL arranged on the image plane side relative to the aperture diaphragm BI satisfy (Expression 3):

$$0.40 < D2/f1 < 1.5 \quad \text{(Expression 3)}.$$

If the value is less than the upper limit in the above expression, an increase in total length of the optical unit is prevented, and if the value exceeds the lower limit in the above expression, a ghost is inconspicuous because the ghost is out of focus, and impossibility of focus adjustment is prevented because a back focal length does not become too small.

Note that the optical unit 10 more preferably satisfies (Expression 3A) and particularly preferably satisfies (Expression 3B) to make the aforementioned effects more prominent:

$$0.45 < D2/f1 < 1.3 \quad \text{(Expression 3A); and}$$

$$0.50 < D2/f1 < 1.1 \quad \text{(Expression 3B)}.$$

<Condition 4>

Furthermore, in the optical unit, a distance D from the aperture diaphragm BI to the image plane and a distance D1 from the aperture diaphragm BI to each of the coating surfaces satisfy (Expression 4):

$$0.20 < D1/D < 0.75 \quad \text{(Expression 4)}.$$

If the value is within the range of the above expression, diffracted light is hard to return to the image plane, and thus ghost is hard to be generated.

Note that the optical unit more preferably satisfies (Expression 4A) and particularly preferably satisfies (Expression 4B) to make the aforementioned effect more prominent:

$$0.25 < D1/D < 0.73 \quad \text{(Expression 4A); and}$$

$$0.50 < D1/D < 0.72 \quad \text{(Expression 4B)}.$$

<Condition 5>

An angle of reflection of diffracted light from the image plane of the CCD 33 depends on the pixel pitch p. Thus, in the optical unit, the rear lens group RL is preferably a positive lens group, each of the coating surfaces is preferably arranged on the image plane side relative to the rear lens group RL, and the distance D1 from the aperture diaphragm BI to each of the coating surfaces and the pixel pitch p of the image pickup device preferably satisfy (Expression 5):

$$0.2 < D1/(p \times 1000) < 2.5 \quad \text{(Expression 5)}.$$

If the value is within the range in the above expression, diffracted light does not return to the image plane and thus no ghost is generated.

Note that the optical unit more preferably satisfies (Expression 5A) and particularly preferably satisfies (Expression 5B) to make the aforementioned effect more prominent:

$$0.5 < D1/(p \times 1000) < 2.0 \quad \text{(Expression 5A); and}$$

$$0.9 < D1/(p \times 1000) < 1.8 \quad \text{(Expression 5B)}.$$

<Condition 6>

An optical unit in which a parallel plate including coating surfaces is arranged on the object side of an aperture diaphragm BI can prevent a periodic pattern ghost caused by light reflected by the CCD 33; however, conversely, an ordinary ghost caused by, e.g., reflection between optical surfaces is easily generated. Furthermore, in an optical unit with a large angle of view, an angle of a light beam on the object side relative to the aperture diaphragm BI falling on each of the coating surfaces tends to be large, and an efficiency of laser light cut-off may be lowered depending on the angular characteristic of the laser cut-off film.

On the other hand, an optical unit in which a parallel plate is arranged on the image plane side relative to an aperture diaphragm BI and a coating surface of a laser cut-off film is present only on each of surfaces of the parallel plate is preferable because the aforementioned problem does not occur.

Furthermore, it is preferable that the optical unit includes an infrared absorption filter F. In particular, an optical unit in which coating surfaces of laser cut-off films are present only on the infrared absorption filter, which is a parallel plate, is preferable because the laser cut-off films do not provide a large change to an image formation magnification (paraxial linear magnification β) and a focal position for a ghost optical path.

Here, numeral values of the optical units 10, 10A and 10B according to the embodiments for (Expression 1) to (Expression 5) are indicated in (Table 4). Note that the values of the optical units 10a and 10b are partly similar to those of the optical unit 10.

Furthermore, it is clear that each of an optical unit including an LD laser cut-off film FB only on a surface on any of the object side and the image plane side of an infrared absorption filter F and an optical unit including a same YAG laser cut-off film FA or a same LD laser cut-off film FB on each of opposite surfaces on the object side and the image plane side has an effect similar to those of each of, e.g., the optical unit 10a and the optical unit 10b.

TABLE 4

| | | Reflecting surface | \|FNO · IH/Δd\| | β · IH/Ds | D2/f1 | D1/D | D1/ (p × 1000) |
|---|---|---|---|---|---|---|---|
| First embodiment | | FA | 0.943 | 0.624 | 0.652 | 0.547 | 1.008 |
| | | FB | 0.985 | 0.624 | 0.571 | 0.604 | 1.112 |
| Second embodiment | Far point | FA | 1.204 | 0.522 | 0.913 | 0.634 | 1.610 |
| | | FB | 1.263 | 0.522 | 0.781 | 0.687 | 1.744 |
| | Near point | FA | 1.160 | 0.522 | 0.913 | 0.634 | 1.610 |
| | | FB | 1.217 | 0.522 | 0.781 | 0.687 | 1.744 |
| Third embodiment | Far point | FA | 1.254 | 0.500 | 1.001 | 0.638 | 1.555 |
| | | FB | 1.322 | 0.500 | 0.845 | 0.695 | 1.692 |
| | Near point | FA | 1.208 | 0.500 | 1.001 | 0.638 | 1.555 |
| | | FB | 1.273 | 0.500 | 0.845 | 0.695 | 1.692 |

As indicated in (Table 4), each of the optical units 10, 10A and 10B according to the embodiments and the optical units 10a and 10b according to the modifications satisfies, e.g., (Expression 1) to (Expression 5) and thus, periodic pattern ghost generation was reduced. With the endoscopes according to the embodiments each including the optical unit 10, 10A or 10B or the optical unit 10a or 10b according to the modification, there was no difficulty in observation due to a periodic pattern ghost.

Note that as already described, satisfaction of at least <Condition 1> enables provision of the effects of the present invention, and satisfaction of <Condition 2> simultaneously with <Condition 1> is particularly preferable.

The present invention is not limited to the aforementioned embodiments, various modifications, alterations and the like are possible without departing from the spirit of the present invention.

What is claimed is:

1. An optical unit comprising:
   a plurality of lenses that form an object image on an image plane that is a light-receiving surface of a solid-state image pickup device;

an aperture diaphragm; and an optical member disposed on the image plane side relative to the aperture diaphragm, the optical member including a coating surface resulting from a multi-layer interference film that transmits visible light and cuts off light having a particular wavelength being formed thereon, wherein an F number FNO, a maximum image height IH, and a distance Δd between a paraxial image formation position in a ghost optical path on which a light beam emitted from the aperture diaphragm is reflected by the image plane and further reflected by the coating surface and reaches the image plane again and the image plane satisfy (Expression 1):

$$0.75 < |FNO \cdot IH/\Delta d| < 2.0 \qquad \text{(Expression 1)}.$$

2. The optical unit according to claim 1, wherein the maximum image height IH, a diameter Ds of the aperture diaphragm, and a paraxial linear magnification β for the ghost optical path satisfy (Expression 2):

$$0.1 < \beta \cdot Ds/IH < 1.2 \qquad \text{(Expression 2)}.$$

3. The optical unit according to claim 2, wherein a focal length f1 of a rear lens group arranged on the image plane side relative to the aperture diaphragm, and a distance D2 from the coating surface to the image plane satisfy (Expression 3):

$$0.40 < D2/f1 < 1.5 \qquad \text{(Expression 3)}.$$

4. The optical unit according to claim 3, wherein a distance D from the aperture diaphragm to the image plane, and a distance D1 from the aperture diaphragm to the coating surface satisfy (Expression 4):

$$0.20 < D1/D < 0.75 \qquad \text{(Expression 4)}.$$

5. The optical unit according to claim 4,
wherein the rear lens group arranged on the image plane side relative to the aperture diaphragm, the rear lens group including a plurality of lenses, includes a positive lens group;
wherein the coating surface is present on the image plane side relative to the rear lens group; and
wherein the distance D1 from the aperture diaphragm to the coating surface and a pixel pitch p of the image pickup device satisfy (Expression 5):

$$0.20 < D1/(p \times 1000) < 2.5 \qquad \text{(Expression 5)}.$$

6. The optical unit according to claim 5, wherein the optical member includes a parallel plate arranged on the image plane side relative to the aperture diaphragm, and the coating surface is present only on the parallel plate.

7. The optical unit according to claim 6, wherein coating surfaces resulting from respective multi-layer interference films that cut off light having different wavelengths being formed are present on opposite surfaces of the optical member.

8. The optical unit according to claim 7, wherein the optical member includes an absorption-side filter that cuts off light in an infrared region.

9. An optical unit comprising:
a plurality of lenses that form an object image on an image plane that is a light-receiving surface of a solid-state image pickup device;
an aperture diaphragm; and
an optical member disposed on the image plane side relative to the aperture diaphragm, the optical member including a coating surface resulting from a multi-layer interference film that transmits visible light and cuts off light having a particular wavelength being formed thereon, wherein a rear lens group arranged on the image plane side relative to the aperture diaphragm, the rear lens group including a plurality of lenses, includes a positive lens group;

wherein the coating surface is present on the image plane side relative to the rear lens group; and wherein an F number FNO, a maximum image height IH, and a distance Δd between a paraxial image formation position in a ghost optical path on which a light beam emitted from the aperture diaphragm is reflected by the image plane and further reflected by the coating surface and reaches the image plane again and the image plane, the maximum image height IH, a diameter Ds of the aperture diaphragm, and a paraxial linear magnification β for the ghost optical path, a focal length f1 of the rear lens group arranged on the image plane side relative to the aperture diaphragm, and a distance D2 from the coating surface to the image plane, a distance D from the aperture diaphragm to the image plane, and a distance D1 from the aperture diaphragm to the coating surface, and a pixel pitch p of the image pickup device satisfy (Expression 1 B), (Expression 2B), (Expression 3B), (Expression 4B) and (Expression 5B):

$$0.90 < |FNO \cdot IH/\Delta d| < 1.4 \qquad \text{(Expression 1B)};$$

$$0.35 < \beta \cdot Ds/IH < 0.7 \qquad \text{(Expression 2B)};$$

$$0.50 < D2/f1 < 1.1 \qquad \text{(Expression 3B)};$$

$$0.50 < D1/D < 0.72 \qquad \text{(Expression 4B); and}$$

$$0.9 < D1/(p \times 1000) < 1.8 \qquad \text{(Expression 5B)}.$$

10. An endoscope comprising:
an optical unit including
a plurality of lenses that form an object image on an image plane that is a light-receiving surface of a solid-state image pickup device,
an aperture diaphragm, and
an optical member disposed on the image plane side relative to the aperture diaphragm, the optical member including a coating surface resulting from a multi-layer interference film that transmits visible light and cuts off light having a particular wavelength being formed thereon,
wherein an F number FNO, a maximum image height IH, and a distance Δd between a paraxial image formation position in a ghost optical path on which a light beam emitted from the aperture diaphragm is reflected by the image plane and further reflected by the coating surface and reaches the image plane again and the image plane satisfy (Expression 1), $$0.75 < |FNO \cdot IH/\Delta d| < 2.0 \qquad \text{(Expression 1)};$$

a solid-state image pickup device; and
an illumination optical system.

11. The endoscope according to claim 10, wherein the coating surface cuts off laser light for therapy.

* * * * *